(12) United States Patent
Benkreira et al.

(10) Patent No.: US 10,621,322 B2
(45) Date of Patent: Apr. 14, 2020

(54) PLATFORM FOR DISTINGUISHING HUMAN FROM MACHINE INPUT

(71) Applicant: Capital One Services, LLC, McLean, VA (US)

(72) Inventors: Abdelkadar M'Hamed Benkreira, Washington, DC (US); Michael Mossoba, Arlington, VA (US); Joshua Edwards, Philadelphia, PA (US)

(73) Assignee: Capital One Services, LLC, McLean, VA (US)

( * ) Notice: Subject to any disclaimer, the term of this patent is extended or adjusted under 35 U.S.C. 154(b) by 0 days.

(21) Appl. No.: 16/053,425

(22) Filed: Aug. 2, 2018

(65) Prior Publication Data

US 2020/0042681 A1 Feb. 6, 2020

(51) Int. Cl.
| | | |
|---|---|---|
| *G06F 7/04* | (2006.01) |
| *G06F 15/16* | (2006.01) |
| *G06F 17/30* | (2006.01) |
| *H04L 29/06* | (2006.01) |
| *G06F 21/32* | (2013.01) |
| *G06F 21/36* | (2013.01) |
| *A61B 5/08* | (2006.01) |
| *A61B 5/02* | (2006.01) |

(52) U.S. Cl.
CPC ............... *G06F 21/32* (2013.01); *A61B 5/02* (2013.01); *A61B 5/08* (2013.01); *G06F 21/36* (2013.01); *H04L 63/102* (2013.01); *G06F 2221/2103* (2013.01); *G06F 2221/2133* (2013.01)

(58) Field of Classification Search
CPC .......... G06F 21/31; G06F 21/32; G06F 21/36; G06F 2221/2103; G06F 2221/2133; G06F 7/04; G06F 15/16; G06F 17/30; H04L 63/102; H04L 29/06; A61B 5/02; A61B 5/08
See application file for complete search history.

(56) References Cited

U.S. PATENT DOCUMENTS

| | | | | |
|---|---|---|---|---|
| 2007/0177770 | A1* | 8/2007 | Derchak | G06K 9/00496 382/115 |
| 2009/0055193 | A1* | 2/2009 | Maislos | G06F 21/32 704/273 |
| 2013/0044055 | A1* | 2/2013 | Karmarkar | G06F 3/013 345/158 |

(Continued)

*Primary Examiner* — Trong H Nguyen
*Assistant Examiner* — Amie C. Lin
(74) *Attorney, Agent, or Firm* — Harrity & Harrity, LLP

(57) ABSTRACT

A device transmits an instruction for completing a human authentication challenge, to access a server device. The instruction includes information indicating a biometric parameter to be provided by a user, and information indicating a task, to be performed by the user, for varying the biometric parameter. The device receives a request to validate performance of the task. The device obtains a first measurement of the biometric parameter, provided by the user at a first point in time, and obtains a second measurement of the biometric parameter, provided by the user at a second point in time that is later than the first point in time. The device compares the first measurement and the second measurement, and selectively validates the request, based on a result of comparing the first measurement and the second measurement, to selectively grant access to the server device.

20 Claims, 8 Drawing Sheets

(56) References Cited

U.S. PATENT DOCUMENTS

| | | |
|---|---|---|
| 2013/0267204 A1* | 10/2013 | Schultz .................. H04W 12/06 |
| | | 455/411 |
| 2014/0310764 A1 | 10/2014 | Tippett et al. |
| 2014/0359722 A1 | 12/2014 | Schultz et al. |
| 2015/0109124 A1 | 4/2015 | He et al. |
| 2017/0180348 A1* | 6/2017 | Piccolotto .......... G06K 9/00906 |
| 2018/0261227 A1* | 9/2018 | Blouet .................... G10L 17/08 |

* cited by examiner

PLATFORM FOR DISTINGUISHING HUMAN FROM MACHINE INPUT

BACKGROUND

Challenge-response type of tests may be added to a website for distinguishing humans from potentially harmful robotic software programs, or "bots". Many of these tests, known as Completely Automated Public Turing tests to tell Computers and Humans Apart (CAPTCHAs), challenge an end user to perform a task to prove that the end user is a human. Such tasks are designed to prevent bots from engaging in abusive activities on the website.

SUMMARY

According to some possible implementations, a method may include transmitting, by a processor, an instruction for completing a human authentication challenge, to access a server device, wherein the instruction includes information indicating a biometric parameter to be provided by a user, and information indicating a task, to be performed by the user, for varying the biometric parameter. The method may include receiving, by the processor, a request to validate performance of the task, obtaining, by the processor, a first measurement of the biometric parameter, wherein the first measurement is provided by the user at a first point in time, and obtaining, by the processor, a second measurement of the biometric parameter, wherein the second measurement is provided by the user at a second point in time that is later than the first point in time. The method may include comparing, by the processor, the first measurement and the second measurement, and selectively validating, by the processor, the request, based on a result of comparing the first measurement and the second measurement, to selectively grant access to the server device.

According to some possible implementations, a device may include one or more memories, and one or more processors, communicatively coupled to the one or more memories, to transmit, to a user device, an instruction for completing a human authentication challenge, wherein the instruction includes information indicating a biometric parameter to be provided by a user of the user device, and information indicating a task, to be performed by the user, for varying the biometric parameter. The one or more processors may receive, from the user device, an indication that the task is complete. The one or more processors may determine whether the task is complete, wherein, to determine whether the task is complete, the one or more processors are to obtain a first measurement of the biometric parameter provided by the user, to obtain a second measurement of the biometric parameter provided by the user, wherein the first measurement is provided prior to the second measurement, to compare the first measurement and the second measurement, and to determine that the task is complete when a result of comparing the first measurement and the second measurement satisfies a threshold. The one or more processors may cause an action to be performed based on determining that the task is complete.

According to some possible implementations, a non-transitory computer-readable medium may store instructions that include one or more instructions that, when executed by one or more processors of a device, cause the one or more processors to transmit an instruction for completing a human authentication challenge, to access a server device, wherein the instruction includes information indicating a biometric parameter to be provided by a user, and information indicating a task, to be performed by the user, for varying the biometric parameter. The one or more instructions may cause the one or more processors to receive a request to validate performance of the task, to obtain a first measurement of the biometric parameter provided by the user, and to obtain a second measurement of the biometric parameter provided by the user, wherein the first measurement is provided prior to the second measurement. The one or more instructions may cause the one or more processors to compare the first measurement and the second measurement, may validate the request when a result of comparing the first measurement and the second measurement satisfies a threshold, and may deny validation of the request when the result of comparing the first measurement and the second measurement fails to satisfy the threshold.

DETAILED DESCRIPTION

The following detailed description of example implementations refers to the accompanying drawings. The same reference numbers in different drawings may identify the same or similar elements.

Completely Automated Public Turing tests to tell Computers and Humans Apart (CAPTCHAs) are challenges designed to distinguish humans from automated computer programs, or bots, running on the Internet. The challenges are designed to be solvable by humans, but beyond the capabilities of bots, to defend against undesirable or malicious attacks propagated by bots. Existing, text-based CAPTCHAs, may challenge a user to recognize a word formed by multiple, often overlapping, characters that appear in different fonts and/or styles, as bots have trouble when presented with character segmentation (i.e., identifying the correct location and order of the characters). However, computer models have demonstrated the ability to break or solve such text-based CAPTCHAs, by including character segmentation models based on human vision and systems neuroscience.

Some implementations described herein provide a human authentication platform, by which a user may be instructed to stimulate a biometric parameter for proving that the user is a human, and not a machine (e.g., or an automated computer program running on the machine, etc.), to gain access to a server device. As one example, the user may be instructed to perform, in real-time, a stationary exercise that stimulates the user's heart rate. In this way, the human authentication platform may provide a robust, physically interactive human authentication challenge, that may not be performed by a computer program. In this way, the security associated with protecting a website may improve, as malicious attacks propagated by malicious computer programs may be reduced or mitigated, based on failure of the malicious computer programs to complete the human authentication challenges. In this way, the user may additionally be prompted to perform short bursts of physical activity to break up prolonged periods of time in front of a computer.

Figure 1A:
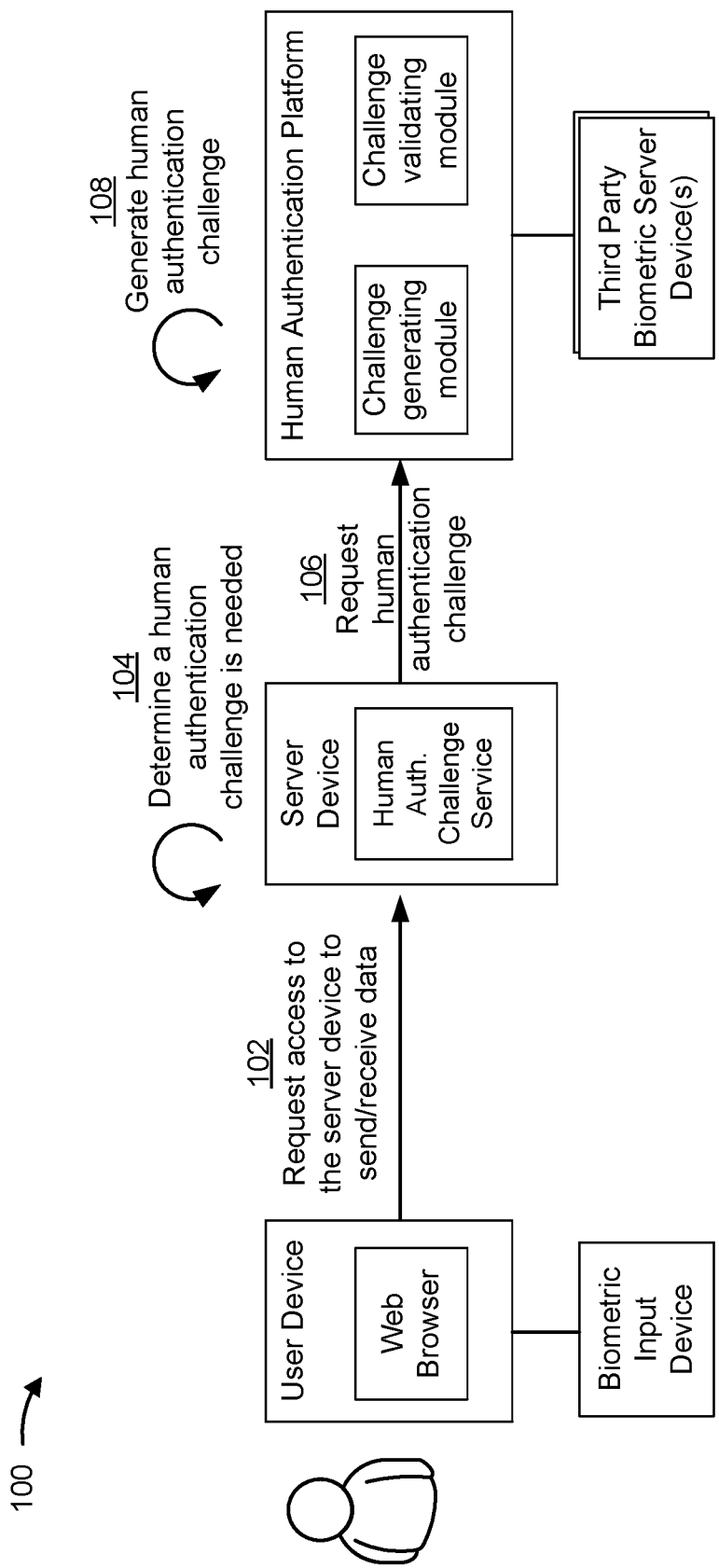
FIGS. 1A-1C are diagrams of an example implementation described herein.
Figure 1B:
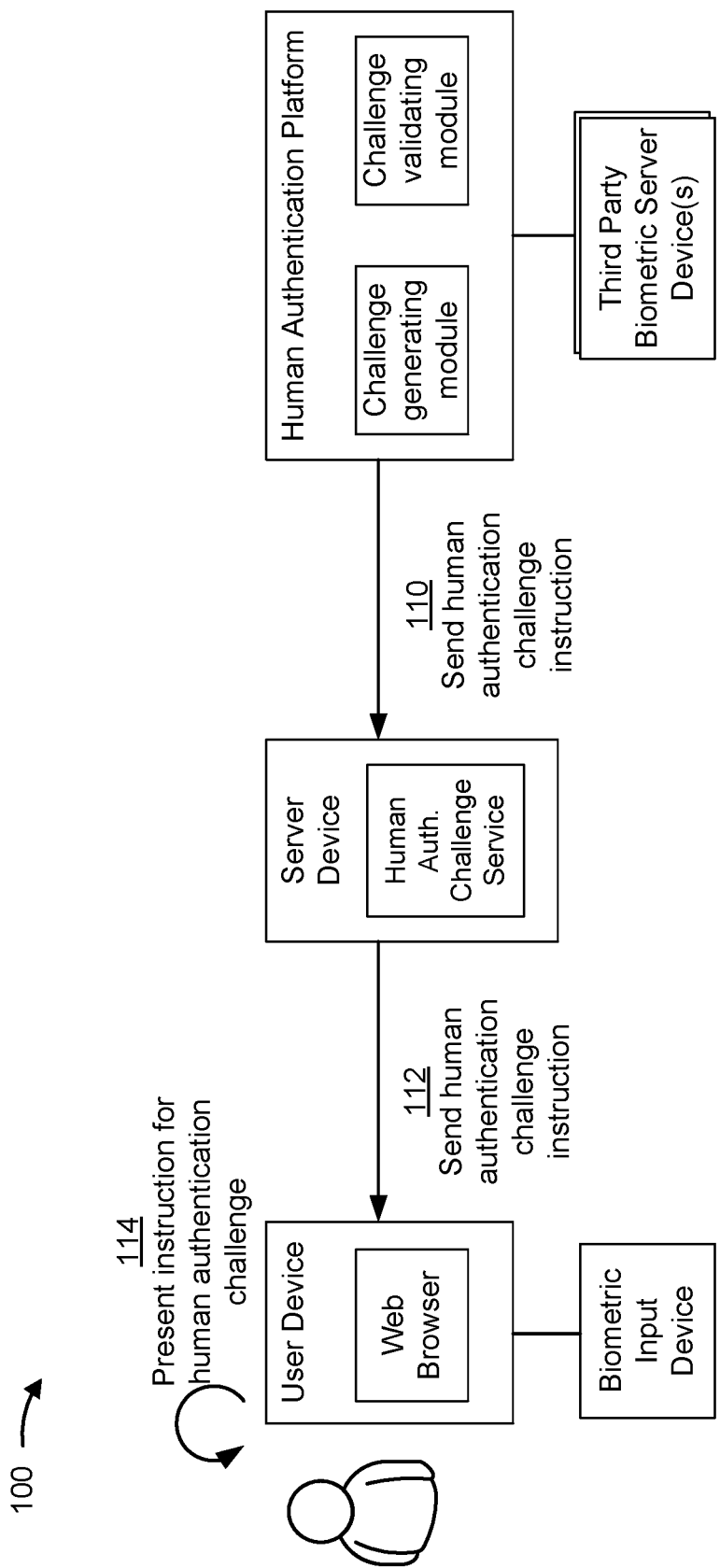
Figure 1C:
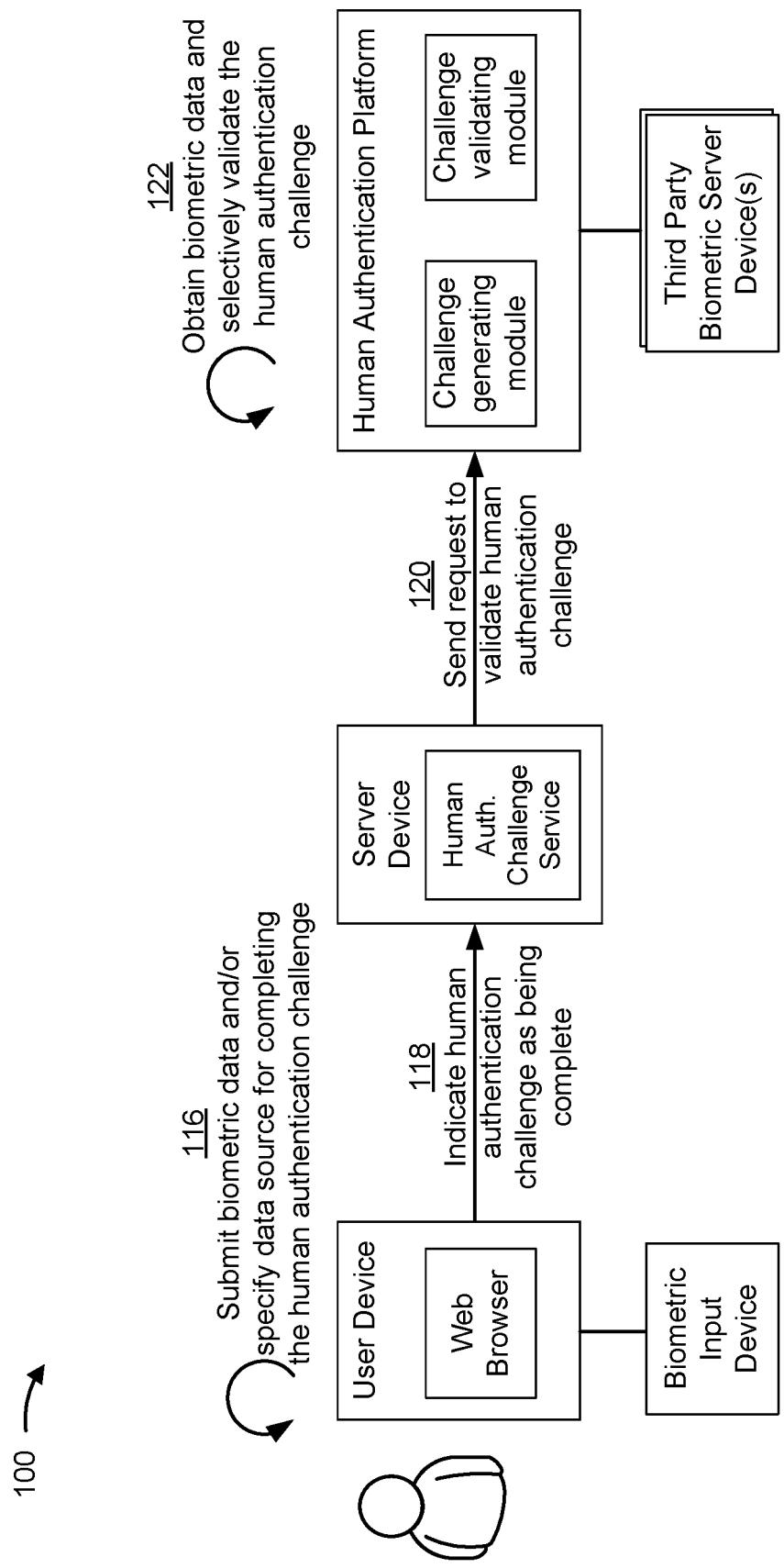

FIGS. 1A-1C are diagrams of an example implementation 100 described herein. As shown in FIGS. 1A-1C, example implementation 100 may include a human authentication platform that interacts with one or more user devices and/or with one or more server devices, as described herein.

As shown in FIG. 1A, and by reference number 102, a user may employ a user device to request access to a server device. In some implementations, the request may include a request to send data to the server device and/or a request to receive data from the server device. For example, the request may include a request to submit data (e.g., upload data, stream data, submit a form, etc.) to the server device, a request to access data (e.g., download data, view data, etc.) from the server device, a request to perform a transaction (e.g., transfer currency, trade a stock, etc.) by way of the server device, a request to make a purchase by way of the server device, and/or the like.

In some implementations, the user may request access to the server device by way of a web browser running on the user device. The user device may include, for example, and without limitation, a smart device, a smart phone, a computer, a wearable computer (e.g., a smart wristwatch, a pair of smart eyeglasses, etc.), and/or the like. In some implementations, the user device may include one or more user interfaces (e.g., a display screen, a keyboard, a touch screen, etc.) by which the user may access the web browser. In some implementations, the server device may include a host device (e.g., a host server device) configured to serve a website that is accessed using the web browser.

As further shown in FIG. 1A, and by reference number 104, the server device may receive the request from the user device, and determine that a human authentication challenge is required or otherwise needed, in order to grant the user device access to the server device. The human authentication challenge may include a challenge that is configured to distinguish a human from a machine, or an automated computing program running on the machine. As an example, the human authentication challenge may include a CAPTCHA, which sets forth a task that is performable (e.g., physically, mentally, etc.) by humans, but beyond the capabilities of computer programs. In some implementations, the human authentication challenge includes an instruction instructing the user to alter (e.g., stimulate) a biometric parameter, such as a heart rate, a respiratory rate, an amount of perspiration, a pulmonary signal, a gait, a body temperature, a skin temperature, a voice attribute, and/or the like, as described herein.

In some implementations, the server device may determine that the human authentication challenge is required based on receiving a request from an untrusted device, based on receiving a request for a new session with a trusted device, and/or the like. In some implementations, the server device may determine that the human authentication challenge is needed based on a count of the request, for example, where the human authentication challenge may be required for every fifth request to access the website hosted by the server device, every tenth request to access the website hosted by the server device, and/or the like. In some implementations, the human authentication challenge may be required based on a number of times the user device accesses and/or attempts to access the server device. For example, where a same user device accesses and/or attempts to access the server device a number of times that satisfies a threshold (e.g., a number of times that satisfies the threshold within a period of time, a number of times that satisfies the threshold regardless of a timing associated with the number of times, and/or the like), the server device may determine that the human authentication challenge is needed to verify that the user of the user device is a human, and not a machine. In some implementations, the human authentication challenge may be required for random requests to access the website, which may not necessarily be based on the count, the user device, and/or the session. In this way, the ability to detect and/or mitigate possible attacks by automated computer programs, or bots, may increase.

Additionally, or, alternatively, and in some implementations, the server device may determine that the human authentication challenge is needed based on a browser extension implemented by the user device. For example, the user of the user device may obtain a browser extension for the web browser, which prompts the server device to provide or perform the human authentication challenge at various intervals (e.g., at regular or non-regular intervals), by which the user may be challenged, using a human authentication challenge, to stimulate a biometric parameter according to the specified intervals. The human authentication challenges may be different, for example, and specify different biometric parameters to be varied and/or different tasks (e.g., physical exercise, etc.) to be performed to satisfy the challenge. In this way, the user may incorporate deliberate breaks or periods of physical activity or exercise, however brief, at various intervals while interacting with the user device. In some implementations, the web browser may be configured to replace an existing human authentication challenge (e.g., an existing text-based CAPTCHA, an existing image-based CAPTCHA, etc.) associated with a website, with a human authentication challenge that requests stimulation of a biometric parameter, to prompt the user to perform a physical activity. In this way, the user may incorporate deliberate breaks to reduce eye strain and/or prevent repetitive strain injuries associated with prolonged periods of uninterrupted use of the user device.

As further shown in FIG. 1A, and by reference number 106, the server device may request a human authentication challenge from the human authentication platform. In some implementations, the server device may request the human authentication challenge, from the human authentication platform, by way of a human authentication challenge service included with the website being served by the server device. For example, the human authentication challenge service may include a servlet (e.g., a Java servlet, etc.), a plugin, and/or the like, associated with the website. The servlet, plugin, and/or other service mechanism may request the human authentication challenge from the human authentication platform and/or obtain the human authentication challenge from the human authentication platform, in real-time, using a communication protocol, an API call, and/or the like.

As further shown in FIG. 1A, and by reference number 108, the human authentication platform may obtain, or generate, a human authentication challenge based on receiving the request from the server device, or the request from the human authentication challenge service running on the website served by the server device. The human authentication platform may include a challenge generating module configured to generate a human authentication challenge, by which a human user of the user device may be distinguishable from a machine user. The challenge generating module may generate a challenge that includes an instruction for varying (e.g., changing, stimulating, modifying, etc.) a biometric parameter. The instruction may include information indicating the biometric parameter to be provided by the user of the user device, and information indicating a task to be performed, by the user, for varying the biometric parameter. For example, the instruction may identify the biometric parameter to be provided by the user of the user device (e.g., a baseline biometric parameter), and the instruction may additionally specify a task for the user to perform that is intended to vary the biometric parameter specified in the instruction. In some implementations, as described further herein, a challenge validating module of the human authentication platform may validate (e.g., verify, confirm, etc.) the performance of the task based on determining whether a value (e.g., a measurement) of the biometric parameter changes in an expected manner relative to a baseline value of the biometric parameter.

In some implementations, the biometric parameter, identified in the instruction of the human authentication challenge generated by the human authentication platform, may include a pulmonary parameter (e.g., a heart rate, a heart rate variability (e.g., beat-to-beat changes), a pulmonary signal, a blood pressure, etc.), a respiratory parameter (e.g., a respiratory rate, an oxygen level, etc.), a perspiration parameter (e.g., an amount of perspiration, the presence of perspiration, an increase in the presence of perspiration, etc.), a dermal parameter (e.g., a skin moisture content, a skin temperature, etc.), a voice parameter (e.g., a voice pitch, a voice range, a voice volume, etc.), and/or the like. In some implementations, measurements of multiple, biometric parameters (e.g., a combination of pulmonary parameters and respiratory parameters, etc.), and/or measurements of one or more biometric parameters in combination with non-biometric data (e.g., GPS data, image data, video feed, etc.), may be obtained from the user based on the human authentication challenge. In some implementations, the biometric data (e.g., baseline biometric parameter values or measurements, subsequent biometric parameter values or measurements, etc.) associated with the biometric parameter may be obtained and/or measured using a biometric input device and/or a third-party biometric server device, as described herein.

In some implementations, the task identified in the instruction of the human authentication challenge generated by the human authentication platform, may include standing, walking, performing a cardiovascular exercise (e.g., running, jogging, jumping, etc.), performing a stationary exercise (e.g., jogging in place, burpees, push-ups, sit-ups, etc.), performing a vocal exercise (e.g., singing, speaking in different tones, speaking in different volumes, etc.), performing an exercise to generate a pulmonary response (e.g., coughing, holding breath for a specified duration, etc.), and/or the like. The tasks described herein may include some form of physical activity, that is capable of being performed by a human, but not a machine. In this way, the security associated with performing human authentication may increase, and possibly lead to a reduction or mitigation of malicious attacks performed by computer programs.

In some implementations, the instruction of the human authentication challenge, generated by the human authentication platform, may include a quantity, a count, a duration, a measure, and/or the like, associated with the task. For example, the task specified in the instruction of the human authentication challenge may include a length of time associated with performing the task (e.g., run in place for 30 seconds, run in place for 45 seconds, sing for 1 minute, etc.), a count associated with performing the task (e.g., complete 25 jumping jacks, complete 5 burpees, complete 50 sit-ups, cough 3 times, etc.), a general or specific distance associated with performing the task (e.g., run towards the ATM, run away from the computer, jog 1 block, jog 0.5 miles, etc.), and/or the like. Performance of the tasks may be verified using data obtained and/or measured by the biometric input device, the third-party biometric server device, and/or a capture device (e.g., a camera, a sensor, etc.) included with the user device, as described herein.

In some implementations, the human authentication platform may generate the human authentication challenge based on accessing a data structure containing an indication of the tasks, instructions, and/or data associated with the tasks and/or instructions. The data structure may include an indication of the biometric parameter to be measured, an indication of the task for stimulating the biometric parameter, an indication of an amount by which the biometric parameter is to be modified for verification (e.g., a percentage by which to increase or decrease the biometric parameter, an amount by which to increase or decrease the biometric parameter, etc.), indications for any additional metrics associated with the task or instruction (e.g., a count associated with a task, a duration of time to perform a task, etc.), and/or the like. The human authentication platform may generate the human authentication challenge based on rotating instructions contained in the data structure, or using a random generating module to randomly generate instructions based on the data contained in the data structure. Upon generating the challenge, the human authentication platform may retain the information required to validate completion of the challenge, and only transmit, to the user, the instruction for completing the human authentication challenge. As described below, the human authentication platform may obtain the biometric data provided by the user of the user device, and compare the biometric data to the information required to validate completion of the challenge. In this way, the human authentication platform may selectively grant the user device access to the server device, based on a result of the comparison.

Turning now to FIG. 1B, and as shown by reference number 110, the human authentication platform may transmit the instruction for performing the human authentication challenge towards the user device. The instruction may include information indicating the biometric parameter to be provided by the user of the user device, information indicating the task to be performed for altering the biometric parameter, and any other information relating to the task (e.g., the duration of the task, etc.). The human authentication platform may send the instruction to the server device, or to the human authentication challenge service running on the website being served by the server device, using a signal communication protocol, an API interface, and/or the like.

As further shown in FIG. 1B, and by reference number 112, the server device may receive the instruction for the human authentication challenge, and transmit the instruction to the user device. In some implementations, the instruction may be transmitted to the user device by way of the web browser running on the user device. The instruction may be communicated using an IP protocol, an HTTP communication, and/or the like.

As further shown in FIG. 1B, and by reference number 114, the user device may present the instruction to complete the human authentication challenge, to the user. The user device may prompt the user, using the instruction, to complete the challenge by submitting the biometric parameter and performing the task to alter the biometric parameter. In some implementations, the instruction may be displayed to the user by way of a user interface associated with the user device. The instruction may be transmitted for display on the user device as a pop-up window or box, a notification, an electronic message, an SMS text message, and/or the like. In some implementations, the instruction may be sent as an audio message or in an audio format. In this way, the human authentication platform may perform human authentication for a larger sized audience of users.

Turning now to FIG. 1C, and as shown by reference number 116, the user of the user device may submit biometric data associated with the biometric parameter identified in the instruction and/or specify a data source, from which the human authentication platform may access or obtain the biometric data. For example, and in some implementations, the user may submit an initial measurement (e.g., a baseline measurement) of the biometric parameter using a biometric input device. The user may submit a subsequent measurement of the biometric parameter using the biometric input device, upon completion of the task set forth in the human authentication challenge. Example biometric input devices may include, without limitation, a hand or palm scanner, a wearable device including a biometric input interface (e.g., a heart rate monitor, a respiratory rate monitor, an oxygen level monitor, a Fitbit®, etc.), a smart device including a biometric input interface (e.g., a smart phone, a smart watch, etc.), and/or the like, whereby the user may submit multiple measurements of the biometric parameter for satisfying the human authentication challenge.

In some implementations, the biometric input device includes a wearable device, or a standalone biometric input device comprising one or more sensor devices, such as one or more of an accelerometer (e.g., for obtaining data associated with a heart rate, a pulmonary signal, etc.), a gyroscope (e.g., for obtaining data associated with an orientation of the user to verify performance of a directional exercise, such as push-ups, squats, etc.), a magnetometer (e.g., for obtaining data associated with a position of the user, etc.), a temperature sensor (e.g., for obtaining data associated with a skin temperature, etc.), an optical sensor (e.g., for obtaining data associated with heart rate monitoring, electrocardiogram capabilities, etc.), a chemical sensor (e.g., for obtaining data associated with oxygen levels, sodium levels in perspiration, etc.), an electrochemical sensor (e.g., for obtaining data associated with a chemical composition of an epidermis, etc.), an image sensor (e.g., for obtaining data associated with an image of the user performing a task, etc.), a humidity sensor (e.g., for obtaining data associated with perspiration, etc.), a global positioning sensor (GPS) (e.g., for obtaining data associated with a location of a user, etc.), a galvanic skin response sensor (e.g., for obtaining data associated with an amount of perspiration secretion, etc.), and/or the like. In some implementations, the biometric input device may be electrically connected to the user device and/or paired with the user device, so that the user device may obtain the biometric measurements directly from the biometric input device, and submit the biometric measurements to the human authentication platform for verification.

Additionally, or alternatively, in some implementations, the user may specify a data source from which the human authentication platform may obtain the biometric measurements. In this way, the human authentication platform offers flexibility in obtaining data from multiple different sources (e.g., biometric input devices, third-party biometric server devices, etc.). For example, the user may input, using the user device, a type of wearable (e.g., a Fitbit®, an Apple® watch, etc.), an identifier associated with the wearable, and/or the like. The human authentication platform may access the biometric data from a third-party biometric server device (e.g., a Fitbit® server, etc.) based on the identifier associated with the wearable. Alternatively, the user may supply login credentials for accessing the biometric measurements stored on the third-party biometric server device and/or for opting-in to sharing the biometric measurements. In some implementations, the web browser may include a browser extension, whereby the user may enter the information required to access the third-party biometric server devices storing the biometric measurements, and save the information for future use. In this way, the user may be prompted to enter login credentials one time, which may be re-used multiple times, to access biometric measurements for multiple human authentication challenges.

In some implementations, the data received from the biometric input device, and/or the third-party biometric server device, may be anonymized. For example, the human authentication platform may obtain the biometric measurements for use in verifying that the user is human, and to distinguish human input from machine input. The human authentication challenge may be performed without relying on knowledge of the identity of the user submitting the biometric measurements. In this way, the unauthorized access of personal data associated with the user, by an attacker or malicious entity, may be reduced or prevented. In this way, the human authentication platform may obtain biometric measurements for human verification purposes, without having to store the biometric data and/or obtain information relating to individual's identity. In this way, memory resources may be conserved, as any data obtained for verification purposes may be discarded after verification of a human user. In this way, user privacy may be maintained.

As further shown in FIG. 1C, and by reference number 118, the user may indicate the human authentication challenge as being complete. For example, upon performing the task specified by the instruction, the user may indicate the human authentication challenge as being complete by way of checking a box appearing on the web browser, sending a notification, and/or any other method by which the server device may be notified that the challenge is complete.

As further shown in FIG. 1C, and by reference number 120, the server device, or the human authentication challenge service running on the website being served by the server device, may send a request to validate the human authentication challenge. The request may be received by the human authentication platform.

As further shown in FIG. 1C, and by reference number 122, the human authentication platform may obtain biometric data submitted by the user of the user device to selectively validate the human authentication challenge. The biometric data obtained by the human authentication platform may include an initial, baseline biometric measurement and a subsequent, stimulated biometric measurement. The biometric data may be obtained from the user device, the biometric input device associated with the user device, or the third-party biometric server device. For example, in some implementations, the human authentication platform may obtain the initial and subsequent biometric measurements directly from a hand scanner, a smart device, a wearable, and/or the like. Additionally, or alternatively, the human authentication platform may obtain the initial and subsequent biometric measurements directly from a third-party biometric server device that stores biometric data obtained from the wearable device. The biometric data used to validate the human authentication challenge may include pulmonary data, respiratory data, voice data, perspiration data, and/or the like.

In some implementations, the user may provide access to a non-biometric device or interface, such as a camera, GPS sensor, and/or the like, which may be used in combination with the biometric data to perform the task and/or verify completion of the task. For example, the human authentication platform may obtain biometric data for a pulmonary parameter (e.g., a heart rate), and additionally image data obtained from a camera associated with the user device, to verify movement of the user.

The human authentication platform may include a challenge validating module. In some implementations, the challenge validating module may determine if the human authentication challenge has been completed or performed by a machine user or a human user based on the biometric data obtained from the user device, the biometric input device, and/or the third-party biometric server device. For example, a machine is presumed to be unable to perform, solve, or satisfy the human authentication challenge. Accordingly, if the response to the human authentication challenge stimulates the biometric parameter specified in the instruction sent to the user device, the challenge validating module presumes the challenge as being completed by a human. Upon validating the request, the human authentication platform may allow the user to access the server device by way of the user device. Where the request is not validated, the user of the user device may be denied access to the server device.

In some implementations, the human authentication platform may obtain an initial, baseline biometric measurement and a subsequent biometric measurement. The human authentication platform may compare the baseline measurement and the subsequent measurement for determining whether the challenge was completed. In some implementations, the challenge may be verified when the subsequent measurement is greater than or less than the initial measurement by any amount, no matter how large or small. In some implementations, the challenge may be verified when the subsequent measurement exceeds the initial measurement by a predetermined amount (e.g., a predetermined percentage, a predetermined number, etc.). For example, in some implementations, the human authentication platform may determine whether an amount of change, or difference, between the initial measurement and the subsequent measurement satisfies a threshold. The user device may be allowed to access the server device when the result of comparing the initial measurement and the subsequent measurement satisfies the threshold.

Additionally, or alternatively, the user device may be denied access to the server device if the result of comparing the initial measurement and the subsequent measurement fails to satisfy the threshold. In some implementations, selectively validating the request from the server device includes validating the request when the result of comparing the initial measurement and the subsequent measurement satisfies a threshold, and denying validation of the request when the result of comparing the initial measurement and the subsequent measurement fails to satisfy the threshold.

As an example, the human authentication platform may generate a challenge including an instruction for the user to jog in place for 20 seconds to elevate a heart rate above a baseline measurement. The user may receive the instruction and submit, in real-time, information identifying a wearable device to the human authentication platform. The human authentication platform may identify a third-party server device that stores the data obtained from the wearable device based on the information identifying the wearable device. The human authentication platform may obtain the baseline measurement of the user's heart rate from the third-party server device, and obtain a subsequent, real-time measurement of the user's heart rate based on the user indicating the challenge as being complete. As the baseline measurement may be provided prior to the subsequent measurement, the human authentication platform may, optionally, obtain timestamp information for use in determining the baseline measurement. The human authentication platform may obtain and compare the baseline heart rate data and the subsequent heart rate data. Where the subsequent heart rate data exceeds the baseline data (e.g., by any amount, by a predetermined amount, etc.), the human authentication platform may validate the request and grant the user device access to the server device. Where the subsequent heart rate data fails to exceed the baseline data, the human authentication platform may deny the request and deny the user device access to the server device.

In some implementations, the human authentication platform may validate and grant a request by way of examining the biometric measurements to determine that the input is from a human user, and instructing the server device to allow the user device access to the server device. In some implementations, the human authentication platform may deny the request by way of examining the biometric measurements, determining that the biometric measurements may not be obtained from a human user, and instructing the server device to deny the user device access to the server device. A request may be denied, for example, where the human authentication platform could not obtain biometric measurements, where the human authentication platform could not obtain biometric measurements from a reliable source (e.g., by way of the user device providing or presenting authentication information to access verifiable third-party biometric server device, etc.), where the human authentication platform could not verify that the biometric measurements had changed upon the user device indicating a task as being complete, and/or the like. In some implementations, where a request to validate the human authentication challenge is denied, the user may be provided with a second chance at completing the human authentication challenge, the user may be presented with a new human authentication challenge, and/or the like. In some implementations, the user may be denied access to the server device for a predetermined amount of time, after which, the user may be allowed another chance to complete a human authentication challenge. In some implementations, the user may be denied access until a time at which the user may be verified as human. In some implementations, for example, where a user may be incapable of performing a task, the user may be presented with an option to choose a different task (e.g., from a list of tasks) to perform.

As another example, the human authentication platform may generate a challenge that includes an instruction for the user to rub the user's hands together for 20 seconds. In some implementations, a user interface of the user device prompting the user to perform the challenge, may include a count down, or timer by which the user may perform the task. The human authentication platform may obtain a baseline measurement of the user's hand temperature (e.g., before the user performs the task of rubbing the user's hands together for 20 seconds) and a subsequent measurement of the user's hand temperature after the user performs the task. The request to validate the human authentication challenge may be validated where the temperature of the user's hands increases based on comparing the baseline measurement and the subsequent measurement, and the server device may grant access to the user device. In some implementations, the human authentication platform may validate the request based on detecting a decrease in the temperature of the user's hands. For example, the baseline measurement of the user's hand temperature may be obtained at a time at which the user may have just completed rubbing the user's hands, and the subsequent temperature may be obtained 20 seconds after the user completed rubbing the user's hands together. In this way, decreases in biometric measurements may be used to validate requests, in addition to, and/or as an alternative to increases in biometric measurements.

As another example, the human authentication platform may generate a challenge including an instruction for the user to cough three times. The user coughing three times may generate a unique pulmonary signal or response. The human authentication platform may prompt the user to submit (e.g., using a wearable device) a baseline measurement of the pulmonary signal, and a subsequent measurement for comparing to the baseline measurement. The human authentication platform may obtain the baseline measurement and the subsequent measurement to selectively validate the request. The request may be validated where the unique pulmonary signal is detected based on comparing the baseline measurement and the subsequent measurement.

While the implementations set forth in FIGS. 1A-1C describe the human authentication platform as performing human authentication to selectively grant access to the server device, the human authentication platform may also perform human authentication to selectively grant access to other devices or structures, such as selectively granting access to an automated teller machine (ATM), a safe, a vault, a secure area of a building, and/or the like.

In this way, the human authentication platform may provide a robust, physically interactive human authentication challenge, that may not be performed by a computer program. In this way, the security associated with protecting a website may improve, as malicious attacks propagated by malicious computer programs may be reduced or mitigated, based on failure of the malicious computer programs to complete the human authentication challenges. In this way, the user may additionally be required to perform short bursts of physical activity to break up prolonged periods of time in front of a computer.

As indicated above, FIGS. 1A-1C are provided merely as an example. Other examples are possible and may differ from what was described with regard to FIGS. 1A-1C.

Figure 2:
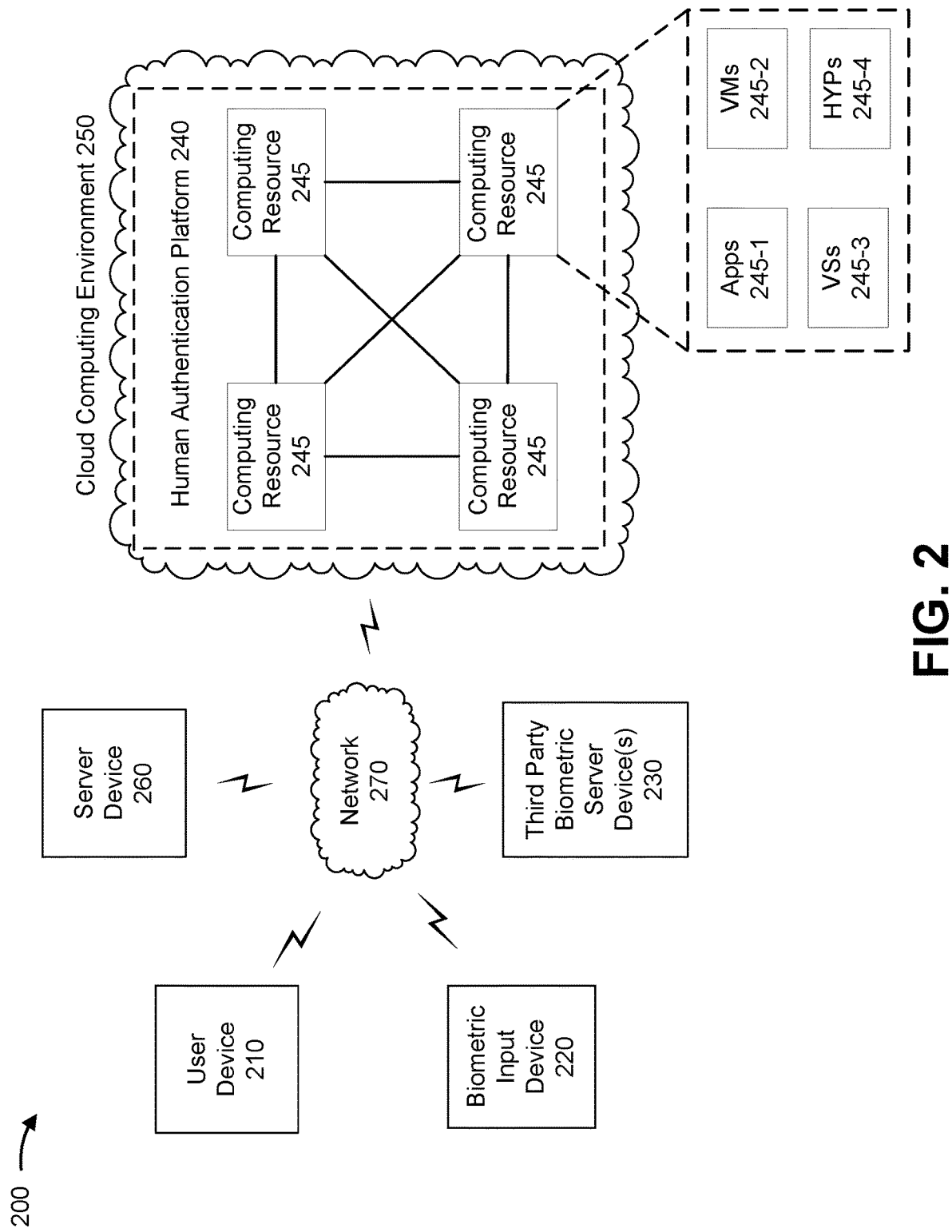
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include a user device 210, a biometric input device 220, a third-party biometric server device 230, human authentication platform 240, a computing resource 245, a cloud computing environment 250, a server device 260, and a network 270. Devices of environment 200 may interconnect via wired connections, wireless connections, or a combination of wired and wireless connections.

User device 210 includes one or more devices capable of sending, receiving, generating, storing, processing, and/or providing information associated with a human authentication challenge that distinguishes human input from machine input. For example, user device 210 may include a communication and/or computing device, such as a mobile phone (e.g., a smart phone, a radiotelephone, etc.), a laptop computer, a tablet computer, a handheld computer, a gaming device, a wearable communication device (e.g., a smart wristwatch, a pair of smart eyeglasses, etc.), or a similar type of device.

Biometric input device 220 includes one or more devices capable of sending, receiving, generating, storing, processing, and/or providing information associated with a human authentication challenge that distinguishes human input from machine input. For example, biometric input device 220 may be a wearable device, such as an activity tracker or health monitor. In various implementations, biometric input device 220 may be a hand or palm scanner, a wearable device that includes a biometric input interface (e.g., a heart rate monitor, a respiratory rate monitor, an oxygen level monitor, a Fitbit®, etc.), a smart device (e.g., a smart phone, a smart watch, etc.) including a biometric input interface (e.g., a finger print scanner, an iris-scanner, a facial recognition interface, etc.), and/or the like, that can measure one or more biometric parameters associated with a user (e.g., of user device 210).

Third-party biometric server device(s) 230 includes one or more devices capable of sending, receiving, generating, storing, processing, and/or providing information associated with a human authentication challenge that distinguishes human input from machine input. In some implementations, third-party biometric server device 230 may be a third-party server device (e.g., a Fitbit® server, an Apple server®, etc.) that may be accessed (e.g., by way of a request or message communicated by a communication protocol, a HTTP request, an API call, etc.) to provide biometric information to human authentication platform 240. For example, biometric server device 230 may store biometric data received from biometric input device 220, and the biometric data may be obtained by human authentication platform 240 to validate a human authentication challenge.

Human authentication platform 240 includes one or more devices capable of sending, receiving, generating, storing, processing, and/or providing information associated with a human authentication challenge that distinguishes human input from machine input. For example, human authentication platform 240 may be a platform implemented by cloud computing environment 250 that may generate, send, receive, and/or validate human authentication challenges for distinguishing human input from machine input. In some implementations, human authentication platform 240 is implemented by computing resources 245 of cloud computing environment 250.

While the example environment 200 indicates that human authentication platform 240 is implemented in a cloud computing environment 250, in some implementations, human authentication platform 240 may be implemented by one or more other types of devices as well, such as a server, computer, laptop computer, tablet computer, handheld computer, or the like.

Cloud computing environment 250 includes an environment that delivers computing as a service, whereby shared resources, services, etc. may be provided to human authentication platform 240 for distinguishing human input from machine input. Cloud computing environment 250 may provide computation, software, data access, storage, and/or other services that do not require end-user knowledge of a physical location and configuration of a system and/or a device that delivers the services. As shown, cloud computing environment 250 may include human authentication platform 240 and computing resources 245.

Computing resource 245 includes one or more personal computers, workstation computers, server devices, or another type of computation and/or communication device. In some implementations, computing resource 245 may host human authentication platform 240. The cloud resources may include compute instances executing in computing resource 245, storage devices provided in computing resource 245, data transfer devices provided by computing resource 245, etc. In some implementations, computing resource 245 may communicate with other computing resources 245 via wired connections, wireless connections, or a combination of wired and wireless connections.

As further shown in FIG. 2, computing resource 245 may include a group of cloud resources, such as one or more applications ("APPs") 245-1, one or more virtual machines ("VMs") 245-2, virtualized storage ("VSs") 245-3, one or more hypervisors ("HYPs") 245-4, or the like.

Application 245-1 includes one or more software applications that may be provided to or accessed by user device 210. Application 245-1 may eliminate a need to install and execute the software applications on user device 210, biometric input device 220, third-party server device 230, and/or the like. For example, application 245-1 may include software associated with human authentication platform 240 and/or any other software capable of being provided via cloud computing environment 250. In some implementations, one application 245-1 may send/receive information to/from one or more other applications 245-1, via virtual machine 245-2.

Virtual machine 245-2 includes a software implementation of a machine (e.g., a computer) that executes programs like a physical machine. Virtual machine 245-2 may be either a system virtual machine or a process virtual machine, depending upon use and degree of correspondence to any real machine by virtual machine 245-2. A system virtual machine may provide a complete system platform that supports execution of a complete operating system ("OS"). A process virtual machine may execute a single program, and may support a single process. In some implementations, virtual machine 245-2 may execute on behalf of a user (e.g., user device 210, server device 220, etc.), and may manage infrastructure of cloud computing environment 250, such as data management, synchronization, or long-duration data transfers.

Virtualized storage 245-3 includes one or more storage systems and/or one or more devices that use virtualization techniques within the storage systems or devices of computing resource 245. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 245-4 provides hardware virtualization techniques that allow multiple operating systems (e.g., "guest operating systems") to execute concurrently on a host computer, such as computing resource 245. Hypervisor 245-4 may present a virtual operating platform to the guest operating systems, and may manage the execution of the guest operating systems. Multiple instances of a variety of operating systems may share virtualized hardware resources.

Server device 260 includes one or more devices capable of storing, processing, and/or routing information associated with human authentication challenges for distinguishing human input from machine input. In some implementations, server device 260 may include a server device having a communication interface that allows server device 260 to receive information from and/or transmit information to other devices in environment 200.

Network 270 may include one or more wired and/or wireless networks. For example, network 270 may include a cellular network (e.g., a long-term evolution (LTE) network, a code division multiple access (CDMA) network, a 3G network, a 4G network, a 5G network, another type of next generation network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
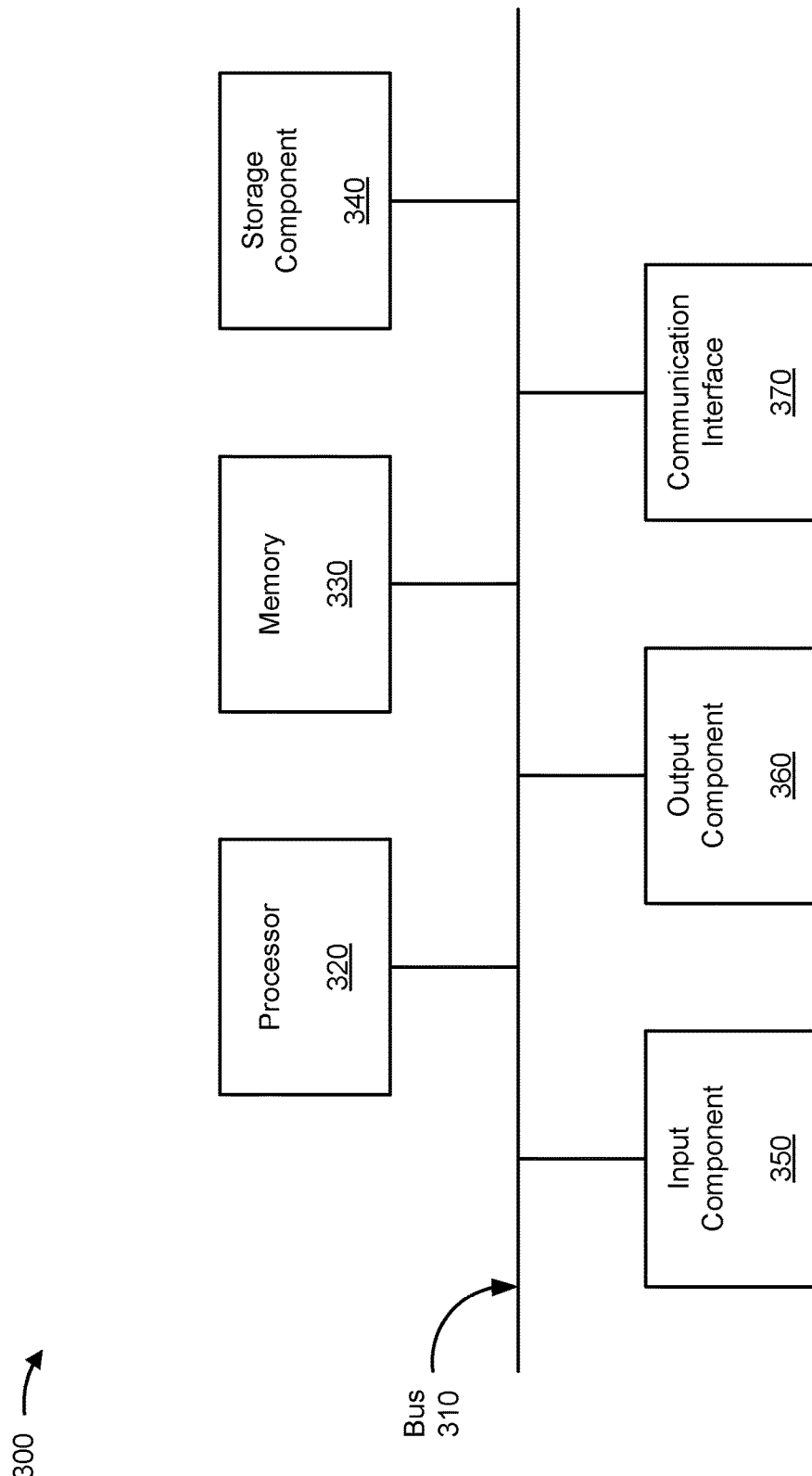
FIG. 3 is a diagram of example components of one or more devices of FIG. 2.

FIG. 3 is a diagram of example components of a device 300. Device 300 may correspond to user device 210, biometric input device 220, third-party biometric server device 230, human authentication platform 240, computing resource 245, and/or server device 260. In some implementations, user device 210, biometric input device 220, third-party biometric server device 230, human authentication platform 240, computing resource 245, and/or server device 260 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes based on processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
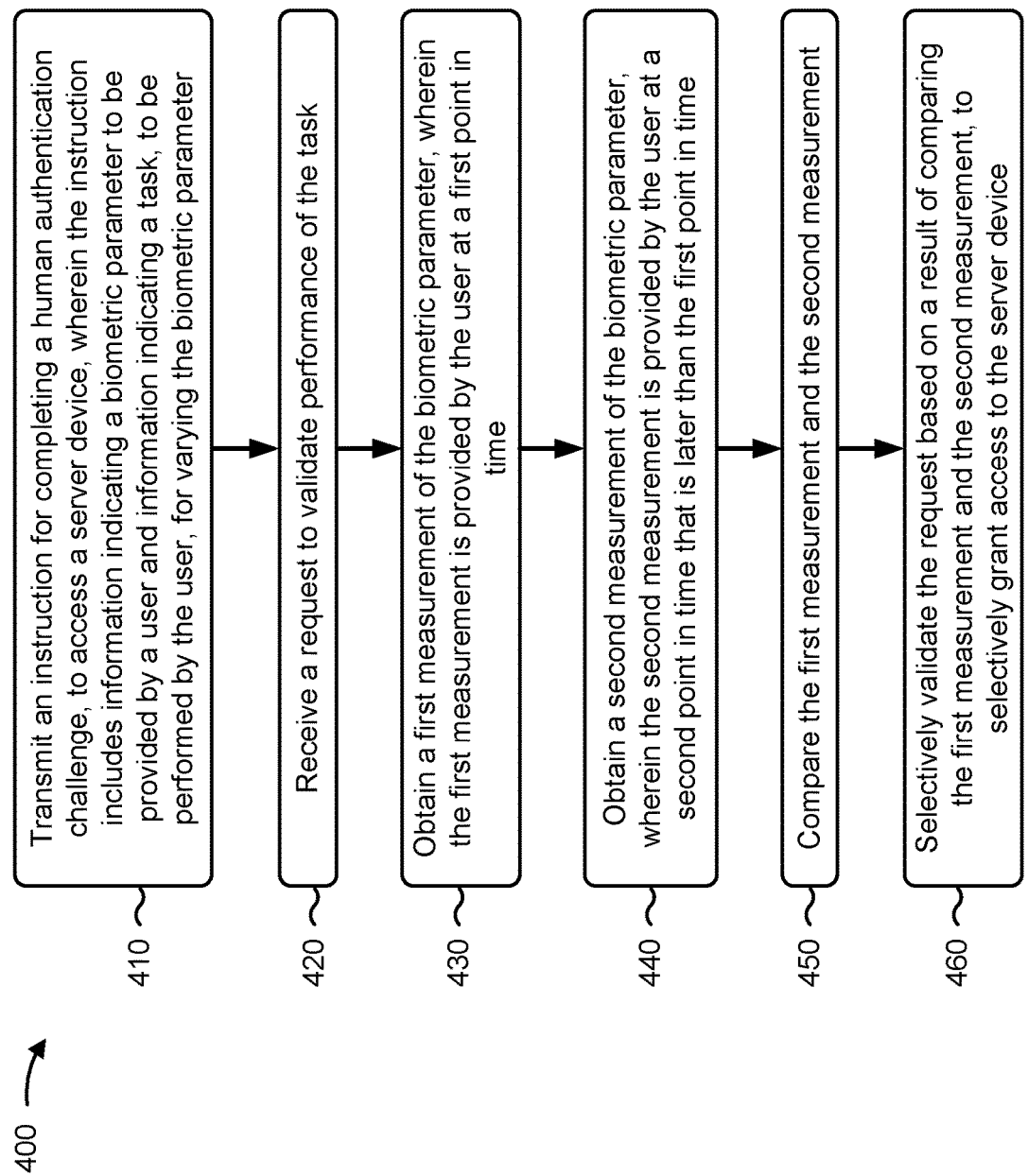
FIG. 4 is a flow chart of an example process for providing a human authentication challenge that distinguishes human input from machine input.

FIG. 4 is a flow chart of an example process 400 for providing a human authentication challenge that distinguishes human input from machine input. In some implementations, one or more process blocks of FIG. 4 may be performed by a human authentication platform (e.g., human authentication platform 240) and/or a computing resource (e.g., computing resource 245) associated with the human authentication platform. In some implementations, one or more process blocks of FIG. 4 may be performed by another device or a group of devices separate from or including human authentication platform (e.g., human authentication platform 240), such as a user device (e.g., user device 210), a biometric input device (e.g., biometric input device 220), a third-party biometric server device (e.g., third-party biometric server device(s) 230), and a server device (e.g., server device 260).

As shown in FIG. 4, process 400 may include transmitting an instruction for completing a human authentication challenge, to access a server device, wherein the instruction includes information indicating a biometric parameter to be provided by a user, and information indicating a task, to be performed by the user, for varying the biometric parameter (block 410). For example, the human authentication platform (e.g., using processor 320, memory 330, storage component 340, output component 360, communication interface 370, and/or the like) may transmit an instruction for completing a human authentication challenge, to access a server device, as described above in connection with FIGS. 1A-1C. In some implementations, the instruction may include information indicating a biometric parameter to be provided by a user, and information indicating a task, to be performed by the user, for varying the biometric parameter.

As further shown in FIG. 4, process 400 may include receiving a request to validate performance of the task (block 420). For example, the human authentication platform (e.g., using processor 320, memory 330, storage component 340, input component 350, communication interface 370, and/or the like) may receive a request to validate performance of the task, as described above in connection with FIGS. 1A-1C.

As further shown in FIG. 4, process 400 may include obtaining a first measurement of the biometric parameter, wherein the first measurement is provided by the user at a first point in time (block 430). For example, the human authentication platform (e.g., using processor 320, memory 330, storage component 340, input component 350, communication interface 370, and/or the like) may obtain a first measurement of the biometric parameter, as described above in connection with FIGS. 1A-1C. In some implementations, the first measurement may be provided by the user at a first point in time.

As further shown in FIG. 4, process 400 may include obtaining a second measurement of the biometric parameter, wherein the second measurement is provided by the user at a second point in time that is later than the first point in time (block 440). For example, the human authentication platform (e.g., using processor 320, memory 330, storage component 340, input component 350, communication interface 370, and/or the like) may obtain a second measurement of the biometric parameter, as described above in connection with FIGS. 1A-1C. In some implementations, the second measurement may be provided by the user at a second point in time that is later than the first point in time.

As further shown in FIG. 4, process 400 may include comparing the first measurement and the second measurement (block 450). For example, the human authentication platform (e.g., using processor 320, memory 330, storage component 340, and/or the like) may compare the first measurement and the second measurement, as described above in connection with FIGS. 1A-1C.

As further shown in FIG. 4, process 400 may include selectively validating the request, based on a result of comparing the first measurement and the second measurement, to selectively grant access to the server device (block 460). For example, the human authentication platform (e.g., using processor 320, memory 330, storage component 340, output component 360, communication interface 370, and/or the like) may selectively validate the request, based on a result of comparing the first measurement and the second measurement, to selectively grant access to the server device, as described above in connection with FIGS. 1A-1C.

Process 400 may include additional implementations, such as any single implementation or any combination of implementations described below and/or in connection with one or more other processes described elsewhere herein.

In some implementations, the human authentication challenge may include a Completely Automated Public Turing test to tell Computers and Humans Apart (CAPTCHA). In some implementations, the biometric parameter may include a pulmonary parameter, a respiratory parameter, and/or a perspiration parameter.

In some implementations, the first measurement or the second measurement may be obtained from a sensor device, and the sensor device may include at least one of an accelerometer, a gyroscope, a magnetometer, a temperature sensor, an optical sensor, a chemical sensor, an electrochemical sensor, an image sensor, a humidity sensor, or a global positioning sensor. In some implementations, the sensor device may be disposed in a wearable device, a mobile device, a biometric input device attached to a computer, or a computer.

In some implementations, the instruction may be transmitted based on a request of a user device to access the server device to submit an electronic form, download content, perform a transaction, or make a purchase. In some implementations, the task may include standing, walking, or performing a stationary exercise.

In some implementations, when selectively validating the request, the human authentication platform may validate the request when the result of comparing the first measurement and the second measurement satisfies a threshold, or deny validation of the request when the result of comparing the first measurement and the second measurement fails to satisfy the threshold.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
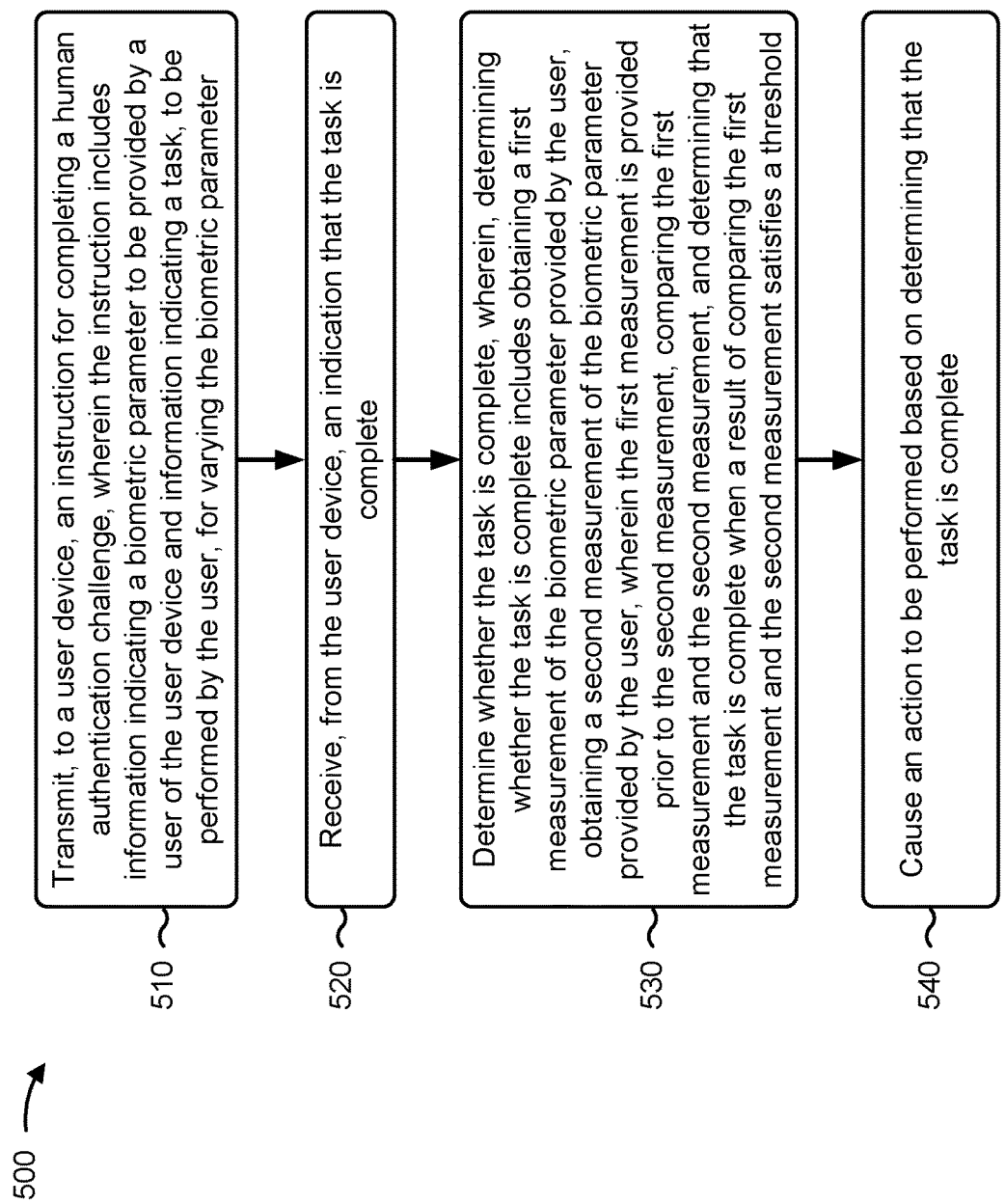
FIG. 5 is a flow chart of an example process for providing a human authentication challenge that distinguishes human input from machine input.

FIG. 5 is a flow chart of an example process 500 for providing a human authentication challenge that distinguishes human input from machine input. In some implementations, one or more process blocks of FIG. 5 may be performed by a human authentication platform (e.g., human authentication platform 240), or a computing resource (e.g., computing resource 245) of the human authentication platform. In some implementations, one or more process blocks of FIG. 5 may be performed by another device or a group of devices separate from or including human authentication platform (e.g., human authentication platform 240), such as a user device (e.g., user device 210), a biometric input device (e.g., biometric input device 220), a third-party biometric server device (e.g., third-party biometric server device(s) 230), and a server device (e.g., server device 260).

As shown in FIG. 5, process 500 may include transmitting, to a user device, an instruction for completing a human authentication challenge, wherein the instruction may include information indicating a biometric parameter to be provided by a user of the user device, and information indicating a task, to be performed by the user, for varying the biometric parameter (block 510). For example, the human authentication platform (e.g., using processor 320, memory 330, storage component 340, output component 360, communication interface 370, and/or the like) may transmit, to a user device, an instruction for completing a human authentication challenge, as described above in connection with FIGS. 1A-1C. In some implementations, the instruction may include information indicating a biometric parameter to be provided by a user of the user device, and information indicating a task, to be performed by the user, for varying the biometric parameter.

As further shown in FIG. 5, process 500 may include receiving, from the user device, an indication that the task is complete (block 520). For example, the human authentication platform (e.g., using processor 320, memory 330, storage component 340, input component 350, communication interface 370, and/or the like) may receive, from the user device, an indication that the task is complete, as described above in connection with FIGS. 1A-1C.

As further shown in FIG. 5, process 500 may include determining whether the task is complete, wherein, to determine whether the task is complete, the human authentication platform may obtain a first measurement of the biometric parameter provided by the user, may obtain a second measurement of the biometric parameter provided by the user, wherein the first measurement is provided prior to the second measurement, may compare the first measurement and the second measurement, and may determine that the task is complete when a result of comparing the first measurement and the second measurement satisfies a threshold (block 530). For example, the human authentication platform (e.g., using processor 320, memory 330, storage component 340, input component 350, communication interface 370, and/or the like) may determine whether the task is complete, as described above in connection with FIGS. 1A-1C. In some implementations, to determine whether the task is complete, the human authentication platform may obtain a first measurement of the biometric parameter provided by the user, may obtain a second measurement of the biometric parameter provided by the user, wherein the first measurement is provided prior to the second measurement, may compare the first measurement and the second measurement, and may determine that the task is complete when a result of comparing the first measurement and the second measurement satisfies a threshold.

As further shown in FIG. 5, process 500 may include causing an action to be performed based on determining that the task is complete (block 540). For example, the human authentication platform (e.g., using processor 320, memory 330, storage component 340, input component 350, output component 360, communication interface 370, and/or the like) may cause an action to be performed based on determining that the task is complete, as described above in connection with FIGS. 1A-1C.

Process 500 may include additional implementations, such as any single implementation or any combination of implementations described below and/or in connection with one or more other processes described elsewhere herein.

In some implementations, the human authentication challenge may include a Completely Automated Public Turing test to tell Computers and Humans Apart (CAPTCHA). In some implementations, the user device may include a mobile device, a wearable device, a computer, a kiosk, and/or an Automated Teller Machine (ATM).

In some implementations, the biometric parameter may include a pulmonary parameter, a respiratory parameter, and/or a perspiration parameter. In some implementations, the pulmonary parameter may include a heart rate, and/or a pulmonary signal. In some implementations, the first measurement or the second measurement may be provided by a wearable device, a mobile device, and/or a biometric input device. In some implementations, the task may include standing, walking, and/or performing a stationary exercise.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

Figure 6:
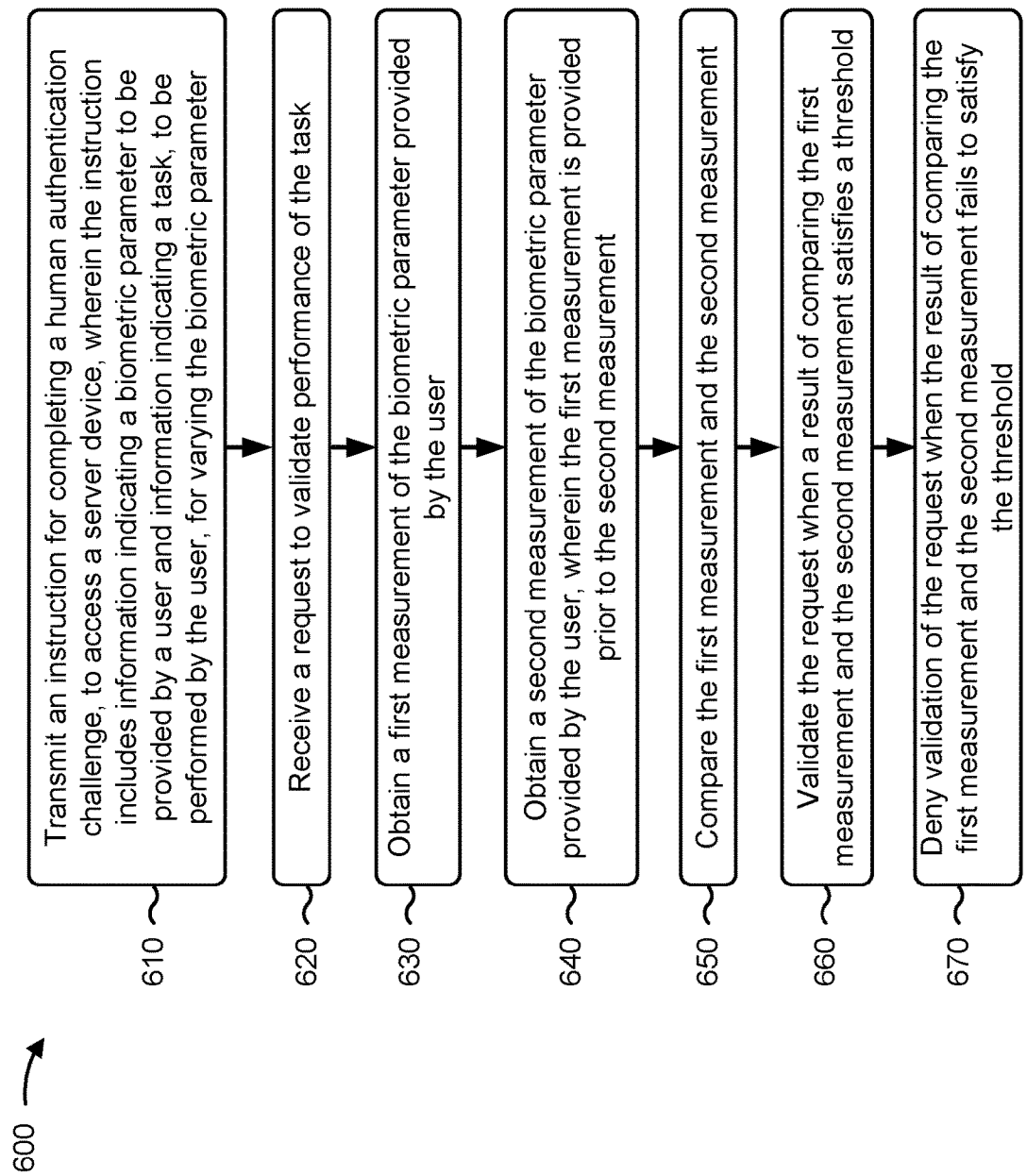
FIG. 6 is a flow chart of an example process for providing a human authentication challenge that distinguishes human input from machine input.

FIG. 6 is a flow chart of an example process 600 for providing a human authentication challenge that distinguishes human input from machine input. In some implementations, one or more process blocks of FIG. 6 may be performed by a human authentication platform (e.g., human authentication platform 240), or a computing resource (e.g., computing resource 245) of the human authentication platform. In some implementations, one or more process blocks of FIG. 6 may be performed by another device or a group of devices separate from or including human authentication platform (e.g., human authentication platform 240), such as a user device (e.g., user device 210), a biometric input device (e.g., biometric input device 220), a third-party biometric server device (e.g., third-party biometric server device(s) 230), and a server device (e.g., server device 260).

As shown in FIG. 6, process 600 may include transmitting an instruction for completing a human authentication challenge, to access a server device, wherein the instruction includes information indicating a biometric parameter to be provided by a user, and information indicating a task, to be performed by the user, for varying the biometric parameter (block 610). For example, the human authentication platform (e.g., using processor 320, memory 330, storage component 340, output component 360, communication interface 370, and/or the like) may transmit an instruction for completing a human authentication challenge, to access a server device, as described above in connection with FIGS. 1A-1C. In some implementations, the instruction may include information indicating a biometric parameter to be provided by a user, and information indicating a task, to be performed by the user, for varying the biometric parameter.

As further shown in FIG. 6, process 600 may include receiving a request to validate performance of the task (block 620). For example, the human authentication platform (e.g., using processor 320, memory 330, storage component 340, input component 350, communication interface 370, and/or the like) may receive a request to validate performance of the task, as described above in connection with FIGS. 1A-1C.

As further shown in FIG. 6, process 600 may include obtaining a first measurement of the biometric parameter provided by the user (block 630). For example, the human authentication platform (e.g., using processor 320, memory 330, storage component 340, input component 350, communication interface 370, and/or the like) may obtain a first measurement of the biometric parameter provided by the user, as described above in connection with FIGS. 1A-1C.

As further shown in FIG. 6, process 600 may include obtaining a second measurement of the biometric parameter provided by the user, wherein the first measurement is provided prior to the second measurement (block 640). For example, the human authentication platform (e.g., using processor 320, memory 330, storage component 340, input component 350, communication interface 370, and/or the like) may obtain a second measurement of the biometric parameter provided by the user, as described above in connection with FIGS. 1A-1C. In some implementations, the first measurement may be provided prior to the second measurement.

As further shown in FIG. 6, process 600 may include comparing the first measurement and the second measurement (block 650). For example, the human authentication platform (e.g., using processor 320, memory 330, storage component 340, input component 350, communication interface 370, and/or the like) may compare the first measurement and the second measurement, as described above in connection with FIGS. 1A-1C.

As further shown in FIG. 6, process 600 may include validating the request when a result of comparing the first measurement and the second measurement satisfies a threshold (block 660). For example, the human authentication platform (e.g., using processor 320, memory 330, storage component 340, output component 360, communication interface 370, and/or the like) may validate the request when a result of comparing the first measurement and the second measurement satisfies a threshold, as described above in connection with FIGS. 1A-1C.

As further shown in FIG. 6, process 600 may include denying validation of the request when the result of comparing the first measurement and the second measurement fails to satisfy the threshold (block 670). For example, the human authentication platform (e.g., using processor 320, memory 330, storage component 340, output component 360, communication interface 370, and/or the like) may deny validation of the request when the result of comparing the first measurement and the second measurement fails to satisfy the threshold, as described above in connection with FIGS. 1A-1C.

Process 600 may include additional implementations, such as any single implementation or any combination of implementations described below and/or in connection with one or more other processes described elsewhere herein.

In some implementations, the human authentication platform may perform a first action when the request is validated, and may perform a second action when the request is denied validation. In some implementations, the first action may include providing access to a service provided by the server device, and the second action may include denying access to the service provided by the server device. In some implementations, the biometric parameter may include a pulmonary parameter, a respiratory parameter, and/or a perspiration parameter. In some implementations, the task may include standing, walking, and/or performing a stationary exercise.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

Some implementations described herein provide human authentication platform 240, by which a user may be instructed to stimulate a biometric parameter for proving that the user is a human, and not a machine (e.g., or an automated computer program running on the machine, etc.), to gain access to server device 260. As one example, the user may be instructed to perform, in real-time, a stationary exercise that stimulates the user's heart rate. In this way, human authentication platform 240 may provide a robust, physically interactive human authentication challenge, that may not be performed by a computer program. In this way, the security associated with protecting a website may improve, as malicious attacks propagated by malicious computer programs may be reduced or mitigated, based on failure of the malicious computer programs to complete the human authentication challenges. In this way, the user may additionally be prompted to perform short bursts of physical activity to break up prolonged periods of time in front of a computer.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, or the like.

Certain user interfaces have been described herein and/or shown in the figures. A user interface may include a graphical user interface, a non-graphical user interface, a text-based user interface, or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method, comprising:
    transmitting, by a processor, an instruction for completing a Completely Automated Public Turing test to tell Computers and Humans Apart (CAPTCHA), to access a server device,
        wherein the instruction includes:
            information indicating a biometric parameter to be provided by a user,
                the biometric parameter including at least one of:
                    a pulmonary parameter, a respiratory parameter, or a perspiration parameter, and
            information indicating a task, to be performed by the user, for varying the biometric parameter,
                the task being associated with a threshold biometric response that is expected based on the user performing the task;
    receiving, by the processor, a request to validate performance of the task;
    obtaining, by the processor, a baseline measurement of the biometric parameter,
        wherein the baseline measurement is provided by the user at a first point in time after the instruction for completing the CAPTCHA is transmitted;
    obtaining, by the processor, a stimulated measurement of the biometric parameter,
        wherein the stimulated measurement is provided by the user at a second point in time that is later than the first point in time;
    determining, by the processor, a change in the biometric parameter based on comparing the baseline measurement and the stimulated measurement;
    determining, by the processor, whether the change in the biometric parameter exceeds the threshold biometric response that is expected based on the user performing the task; and
    validating, by the processor, the request, when the change in the biometric parameter exceeds the threshold biometric response, to grant access to the server device.

2. The method of claim 1, wherein the baseline measurement or the stimulated measurement are obtained from a sensor device, and
    wherein the sensor device includes at least one of:
        an accelerometer,
        a gyroscope,
        a magnetometer,
        a temperature sensor,
        an optical sensor,
        a chemical sensor,
        an electrochemical sensor,
        an image sensor,
        a humidity sensor, or
        a global positioning sensor.

3. The method of claim 2, wherein the sensor device is disposed in:
    a wearable device,
    a mobile device,
    a biometric input device attached to a computer, or
    a computer.

4. The method of claim 1, wherein the instruction for completing the CAPTCHA is transmitted based on a request of a user device to access the server device to:
  submit an electronic form,
  download content,
  perform a transaction, or
  make a purchase.

5. The method of claim 1, wherein the task includes:
  standing,
  walking, or
  performing a stationary exercise.

6. The method of claim 1, further comprising:
  denying validation of the request when the change in the biometric parameter does not exceed the threshold biometric response.

7. The method of claim 1, where transmitting the instruction for completing the CAPTCHA comprises:
  causing the instruction to be displayed on a user interface associated with a user device,
    where the instruction is displayed as one or more of:
      a pop-up window or box,
      a notification,
      an electronic message, or
      an SMS text message.

8. The method of claim 1, wherein the threshold biometric response includes an expected alteration to at least one of:
  a heart rate,
  a respiratory rate, or
  an amount of perspiration.

9. A device, comprising:
  one or more memories; and
  one or more processors, communicatively coupled to the one or more memories, to:
    transmit, to a user device, an instruction for completing a Completely Automated Public Turing test to tell Computers and Humans Apart (CAPTCHA),
      wherein the instruction includes:
        information indicating a biometric parameter to be provided by a user of the user device, the biometric parameter including at least one of: a pulmonary parameter, a respiratory parameter, or a perspiration parameter, and
        information indicating a task, to be performed by the user, for varying the biometric parameter,
          wherein the task is associated with a threshold biometric response that is expected based on the user performing the task;
    receive, from the user device, an indication that the task is complete;
    determine whether the task is complete,
      wherein, to determine whether the task is complete, the one or more processors are to:
        obtain a baseline measurement of the biometric parameter provided by the user,
        obtain a stimulated measurement of the biometric parameter provided by the user, wherein the baseline measurement is provided prior to the stimulated measurement;
        determine a change in the biometric parameter based on comparing the baseline measurement and the stimulated measurement;
        determine whether the change in the biometric parameter exceeds the threshold biometric response that is expected based on the user performing the task; and
        determine that the task is complete when the change in the biometric parameter exceeds the threshold biometric response; and
    cause an action to be performed based on determining that the task is complete.

10. The device of claim 9, wherein the user device includes one of:
  a mobile device,
  a wearable device,
  a computer,
  a kiosk, or
  an Automated Teller Machine (ATM).

11. The device of claim 9, wherein the pulmonary parameter includes one of:
  a heart rate, or
  a pulmonary signal.

12. The device of claim 9, wherein the baseline measurement or the stimulated measurement is provided by one of:
  a wearable device,
  a mobile device, or
  a biometric input device.

13. The device of claim 9, wherein the task includes:
  standing,
  walking, or
  performing a stationary exercise.

14. The device of claim 9, where the one or more processors, when transmitting the instruction for completing the CAPTCHA, are to:
  transmit the instruction as an audio message or in an audio format.

15. The device of claim 9, wherein the threshold biometric response includes an expected alteration to at least one of:
  a heart rate,
  a respiratory rate, or
  an amount of perspiration.

16. A non-transitory computer-readable medium storing program instructions, the program instructions comprising:
  one or more instructions that, when executed by one or more processors, cause the one or more processors to:
    transmit an instruction for completing a Completely Automated Public Turing test to tell Computers and Humans Apart (CAPTCHA), to access a server device,
      wherein the instruction for completing the CAPTCHA includes:
        information indicating a biometric parameter to be provided by a user, the biometric parameter including at least one of: a pulmonary parameter, a respiratory parameter, or a perspiration parameter, and
        information indicating a task, to be performed by the user, for varying the biometric parameter, wherein the task is associated with a threshold biometric response that is expected based on the user performing the task;
    receive a request to validate performance of the task;
    obtain a baseline measurement of the biometric parameter provided by the user;
    obtain a stimulated measurement of the biometric parameter provided by the user, wherein the baseline measurement is provided prior to the stimulated measurement;
    determine a change in the biometric parameter based on comparing the baseline measurement and the stimulated measurement;
    determine whether the change in the biometric parameter exceeds the threshold biometric response that is expected based on the user performing the task;

validate the request when the change in the biometric parameter exceeds the threshold biometric response; and deny validation of the request when the change in the biometric parameter fails to exceed the threshold biometric response.

17. The non-transitory computer-readable medium of claim 16, where the program instructions further comprise:

one or more instructions that, when executed by one or more processors, cause the one or more processors to:
perform a first action when the request is validated; and
perform a second action when the request is denied validation.

18. The non-transitory computer-readable medium of claim 17, wherein:

the first action includes providing access to a service provided by the server device, and the second action includes denying access to the service provided by the server device.

19. The non-transitory computer-readable medium of claim 16, wherein the task includes:

standing, walking, or performing a stationary exercise.

20. The non-transitory computer-readable medium of claim 16, wherein the threshold biometric response includes an expected alteration to at least one of:

a heart rate, a respiratory rate, or an amount of perspiration.

\* \* \* \* \*